United States Patent
Staffler et al.

(10) Patent No.: US 8,234,766 B2
(45) Date of Patent: Aug. 7, 2012

(54) DEVICE AND METHOD FOR RECONDITIONING SLIP RINGS IN A BUILT-IN STATE

(75) Inventors: Herbert Staffler, Fuerstenfeldbruck (DE); Ronald Suchanecki, Munich (DE); Fabian Schuenke, Fuerstenfeldbruck (DE); Harry Schilling, Eichstaett (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 873 days.

(21) Appl. No.: 12/265,071

(22) Filed: Nov. 5, 2008

(65) Prior Publication Data

US 2009/0129555 A1    May 21, 2009

Related U.S. Application Data

(60) Provisional application No. 60/989,252, filed on Nov. 20, 2007.

(30) Foreign Application Priority Data

Mar. 3, 2008  (DE) .......................... 10 2008 000 489

(51) Int. Cl.
*B23P 6/00* (2006.01)
*H05G 1/02* (2006.01)
(52) U.S. Cl. ..................................... 29/402.11; 378/198
(58) Field of Classification Search ............... 29/402.11, 29/402.09, 56.6, 402.01, 402.04, 402.05, 29/402.06, 402.19, 407.04, 407.06, 701, 29/703, 707, 709, 712, 721; 378/198
See application file for complete search history.

(56) References Cited

U.S. PATENT DOCUMENTS

| | | | |
|---|---|---|---|
| 4,782,580 A | 11/1988 | Capioppo et al. | |
| 5,402,461 A | 3/1995 | Kudo | |
| 5,711,195 A | 1/1998 | Koelling | |
| 7,307,367 B2 | 12/2007 | Angerpointner et al. | |
| 2005/0191858 A1 | 9/2005 | Fukunaga et al. | |
| 2007/0035883 A1 | 2/2007 | Katcha et al. | |

FOREIGN PATENT DOCUMENTS

| | | |
|---|---|---|
| AU | 630835 | 8/1992 |
| DE | 1188901 | 3/1965 |
| DE | 8322929 | 12/1983 |
| DE | 102006036420 | 3/2007 |
| FR | 318628 | 10/1902 |
| JP | 3-222654 | 10/1991 |
| JP | 04258373 | * 9/1992 |
| JP | 6-132264 | 5/1994 |
| JP | 7-204192 | 8/1995 |
| JP | 09190210 | * 7/1997 |
| JP | 2004-320839 | 11/2004 |
| JP | 2005-277396 | 10/2005 |
| WO | 00/78216 | 12/2000 |

* cited by examiner

*Primary Examiner* — John C Hong
(74) *Attorney, Agent, or Firm* — Kevin L. Daffer; Daffer McDaniel, LLP

(57) ABSTRACT

A method and a device are provided for reworking or re-machining the surface and, in particular, the slide tracks of a slip ring while the slip ring is in a built-in state in an appliance or machine using the slip ring. The slip ring is rotated by a drive provided in the appliance for rotating the slip ring during normal operation, or by an auxiliary drive, while a surface-removing cutting tool or surface deforming tool held in a tool holder or carrier adapted to be attached to the appliance or machine is applied to the surface of the moving slip ring to re-machine or recondition the surface. The invention avoids the necessity of dismantling the appliance or machine for the purpose of removing the slip ring for repairs.

9 Claims, 2 Drawing Sheets

DEVICE AND METHOD FOR RECONDITIONING SLIP RINGS IN A BUILT-IN STATE

PRIORITY CLAIM

This application claims priority from U.S. Provisional Application No. 60/989,252 filed on Nov. 20, 2007 and German Patent Application 102008000489.8 filed on Mar. 3, 2008.

BACKGROUND OF THE INVENTION

1. Field of the Invention

The invention relates to field refurbishment of slip rings, and in particular to a device and a method for refurbishing, i.e. reconditioning, repairing, or re-working a surface of a slip ring that is a component part of an appliance or machine, with the slip ring remaining in its built-in state in the appliance or machine, specifically in a gantry of a CT scanner (computer tomograph).

2. Description of the Related Art

Slip rings are usually manufactured in a mechanical fabrication workshop and are then built-into an appliance. An appliance of this kind may be, for example, a large machine such as a gantry of a CT scanner. During operation of a slip ring, mechanical wear occurs owing to mechanical friction between a contact brush and a slide track. With slip rings having carbon brushes on metal tracks, abrasion of the carbon brushes alone is substantially greater than abrasion of the slip ring. The carbon brushes are designed so that they can be exchanged relatively easily. However, during a long period of operation, distinct wear of the slip ring itself becomes noticeable. Thus, furrows, grooves, and other cavities may be formed in the surface of a slip ring or its slide tracks. This damage of the surface leads to an increased contact resistance and to an increased wear of the carbon brushes. The same applies in the case of slip rings with metal brushes. Here too, wear of the surface of the slip ring can be observed following an extended period of operation. The damage to the surface may become apparent after a few months or several years, depending upon the operating conditions. Basically, the brushes can be exchanged easily, whilst repair of the slip ring involves relatively large efforts and outlay. Thus, in accordance with the state of the art, a slip ring to be repaired is demounted from the appliance and is machined in a workshop or a manufacturer's fabrication hall, or even replaced with a new slip ring. This has the disadvantage that the appliance is out of operation for a long period of time, and that a relatively time-consuming and laborious exchange of the slip ring must be performed. CT scanners, in particular, must be substantially dismantled for the slip ring to be exchanged. Because the slip rings concerned here, as disclosed in U.S. Pat. No. 4,782,580, have inner diameters of an order of magnitude of 1.5 m and more, it is possible to re-machine them only by means of special and large lathes in specialized workshops.

BRIEF SUMMARY OF THE INVENTION

The invention is based on the object of introducing a method for the repair of damage to a slip ring surface, and in particular of worn slip ring tracks, which reduces the hitherto-needed outlay of time for the repair and also the necessary cost. Furthermore, the invention is intended to set out a device for performing the method, and also an appliance using a slip ring, which is adapted for convenient reconditioning of the slip ring when necessary.

In accordance with the invention, the above objects are achieved by a method for repairing or reconditioning a slip ring built into an appliance for normal operation, by reworking or machining at least partly a surface of the slip ring whilst the slip ring remains in its built-in state in the appliance, comprising the following steps: (a) mounting a tool carrier having a tool for machining the surface of the slip ring on the appliance; (b) rotating the slip ring relative to the tool carrier; and (c) machining the surface of the slip ring with the tool.

Furthermore, in accordance with the invention the above objects are achieved by a device for repairing or reconditioning a slip ring built into an appliance for normal operation, by reworking or machining at least partly a surface of the slip ring whilst the slip ring remains in its built-in state in the appliance, comprising: means or a fixture for mounting the device on the appliance; at least one tool for machining the surface of the slip ring; and a tool carrier for accommodating and holding in a working position the at least one tool.

In accordance with the invention, the above objects are also achieved by an appliance having a slip ring incorporated therein, comprising at least one accommodating means for mounting at least one device to the appliance for repairing or reconditioning the slip ring by reworking or machining at least partly a surface of the slip ring whilst the slip ring remains in its built-in state in the appliance.

DETAILED DESCRIPTION OF PREFERRED EMBODIMENTS

Figure 1:
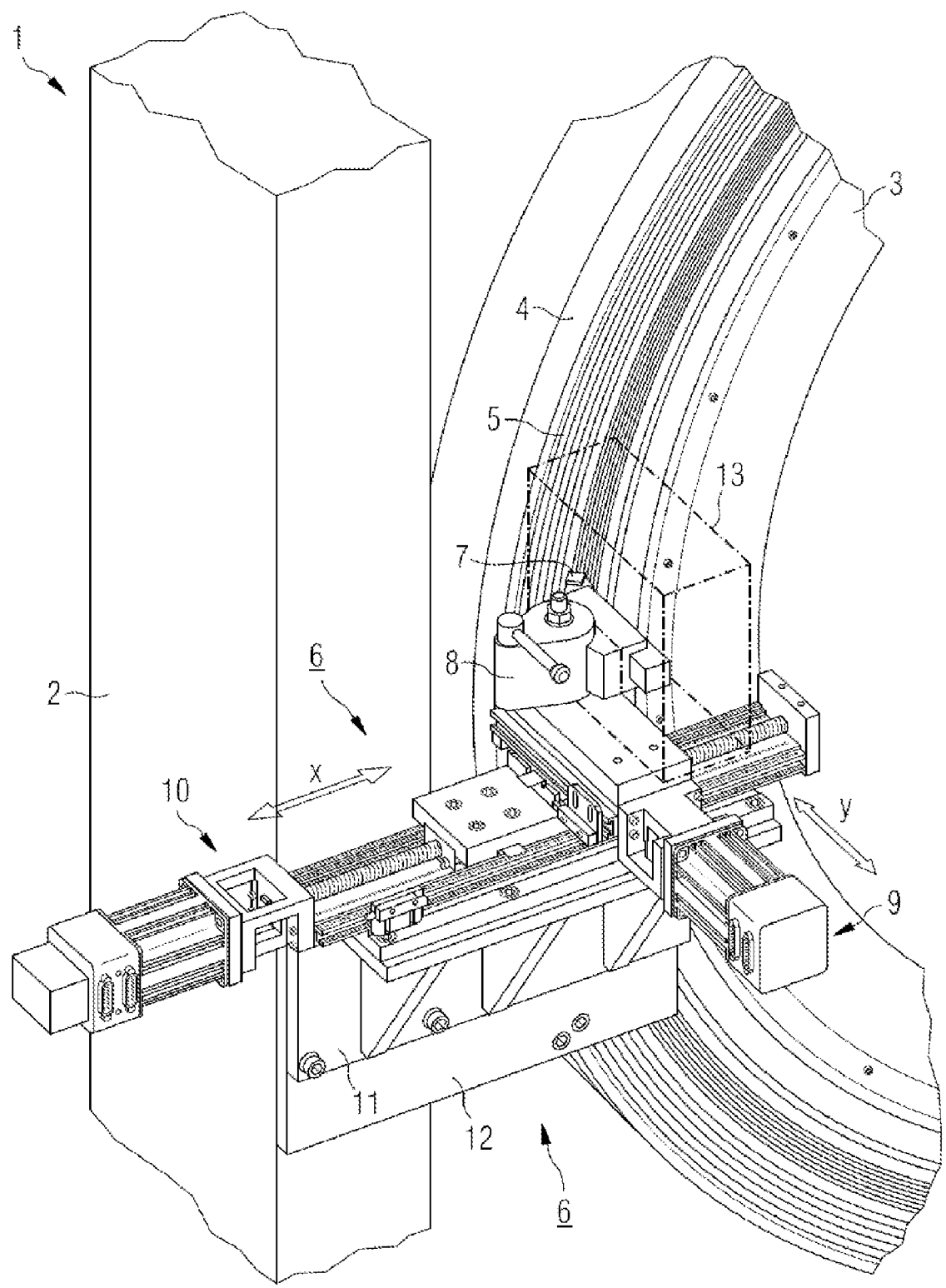
FIG. 1 shows a first arrangement in accordance with the invention.

In the method according to the invention, a slip ring is no longer removed from the appliance, but is machined whilst remaining therein. The terms "working" or "reworking" as used here imply a machining or re-machining of the surface when the slip ring is power-driven to rotate with respect to a tool being used. For this purpose, a tool carrier is mounted on the appliance to hold a tool or tool bit for working the surface of the slip ring and preferably also the slide tracks. A tool of this kind may be, for example, a tool for removing material, or also for deforming the surface. Material removing tools are, for example, cutting tools for chip-removing processing, or also grinding tools. The tools for deforming the surface can be, for example, rollers for roller-burnishing. Basically, also other kinds of tools for working the surface of the slide tracks are possible. However, for this it is of importance that the surface of a slide track to be worked is leveled or smoothed. Optionally a single tool or also a plurality of tools may be employed simultaneously or successively. Thus, for example, a plurality of slide tracks may be worked simultaneously with a plurality of tools. Alternatively, different tools may be employed in temporal or spatial succession.

In order to machine the slide tracks along their entire length, the slip ring is moved relative to the tool. For this, the slip ring itself remains firmly connected with the appliance. The relative movement is therefore effected preferably by a drive of the appliance, which rotates a part of the appliance connected with the slip ring. Of importance to this is a rotary movement about the rotation axis of the slip ring. Thus, for example, in an application in a computer tomograph, the motor normally used for driving the rotary part of the gantry may be used. Preferably the drive for performing the surface working of the slip ring or the slide tracks has a suitable operating mode, such as, for example, an especially low speed. Thus, at a low speed the mechanical vibrations of the appliance can be kept small and the surface quality improved. In the case of an appliance or machine which rotates extremely slowly during normal operation, the drive can have also an operating mode with a higher speed for machining the slide tracks.

With the method according to the invention, the slip ring can be adapted to the appliance in a substantially better way than is possible in a fabrication facility which is separate from the appliance. Thus, for example, the round-running of a slip ring is determined not only by the mechanical tolerances of the appliance and the slip ring itself. It is also affected by the precision of the mounting of the slip ring in the appliance. Now, if the slip ring is reworked in the appliance in accordance with the method of the invention, then the round-running tolerances can be minimized whilst all of these effects are eliminated. Typically, an improvement of the round-running tolerances (radial deviation) by a factor of 10 is possible.

In an advantageous embodiment of the invention, the drive of the appliance can be controlled to have various (rotary) speeds, in order to create respective optimum conditions for machining the surface. Thus, for example, the speed can be controlled by means of suitable software to have a specific speed profile, for example with a slow starting speed that increases up to the machining speed, and with slow braking following the machining. In accordance with the invention, the speed is set according to the requirements of the surface working. Reference is here made expressly to relative movement between the slip ring and the tool. Typically the tool is mounted in a fixed position, optionally on the appliance, or also set-up close to the appliance by means of a stand. The mounting on the appliance can be effected, for example, with screws, bolts, or a quick acting clamp device. During the machining the slip ring is rotated. Alternatively, however, it is also possible to allow the slip ring to rest in fixed position during the working, and to rotate the tool. Similarly, the slip ring and the tool also could be rotated simultaneously, but at different speeds.

In another advantageous embodiment of the invention, the relative movement between the tool and the slip ring, as needed for machining the surface of the slip ring, is effected with an auxiliary drive. Optionally this auxiliary drive can be firmly incorporated in the appliance. Alternatively, however, it also can be mounted on the appliance before working of the surface is begun, and suitably fastened to the appliance with screws, bolts or a quick acting clamp device, and removed from the appliance after the working has ended. This is of particular advantage when the actual drive of the appliance cannot operate in a range of speed which is suitable for re-working the slip ring. Preferably a fixture for accommodating the auxiliary drive is provided on the appliance, so that the auxiliary drive can be simply attached to the appliance with screws, bolts, or a quick acting clamp device. Optionally the auxiliary drive also can be incorporated in a unit together with the tool carrier. Preferably also the speed or speed profile of the auxiliary drive is controlled as previously described.

In the simplest embodiment of the invention, the control or positioning of the tool is effected manually by an operator of the appliance. This operator can then set the tool into an advantageous operating position for working the surface of the individual slide tracks. Furthermore, during the entire working operation the operator can then guide the tool appropriately along the surface of the slip ring or the individual slide tracks. Optionally a semi-automatic operation can be performed in which the operator only aligns the tool on the slide track, and then control of the workpiece on the slide track is effected automatically by a control unit. In the case of a turning tool, for example, the control unit can effect a successive advancement along the entire slide track until the latter has been completely turned. For semi-automatic operation, a simple electrical or also mechanical control unit is sufficient, for example a simple feed controller.

In another embodiment of the invention, control of the position of the tool is effected by means of the tool carrier via an actuating drive. With this, a particularly simple and usually also rapid positioning of the tool is possible. Advantageously, the positioning is effected by program control according to a pre-defined operational plan.

In another embodiment of the invention, common control of the positioning drive of the tool carrier and also the drive of the slip ring is provided. Hereby, for example, first the tool can be put into a suitable position for working, and then the rotation number of the slip ring can be set to a suitable speed for working.

In another advantageous embodiment of the invention, control of the tool is effected by means of a control unit which holds the geometrical data of the slip ring in readiness in a memory. Alternatively, the geometrical data can be retrieved by the control unit also from the appliance into which the slip ring is built. However, advantageously only an identification of the built-in slip ring is retrieved from the appliance. As an alternative to this, the control unit could also retrieve an appliance identification from the appliance and interrogate a data base about the identification and also the geometrical data of the built-in slip ring. In another embodiment, the control unit can also identify the slip ring by other interrogation means, such as a bar code, a transponder, etc. Alternatively, a slip ring or appliance identification also could be input by an operator. Optionally, the control unit can be an external control unit which is provided together with the tool holder only when the slip ring is to be re-worked. As an alternative to this, the control unit also can be already incorporated in an appliance, for example a computer tomograph. Thus, one of the numerous microcontrollers and computers which are present in any case, for example in an appliance such as a computer tomograph, can perform also the task of a control unit. For this purpose only separate software and also suitable interfaces for controlling the tool carrier need be incorporated.

In another advantageous embodiment at least one sensor is provided for identifying at least one slide track. Advantageously, this sensor is incorporated in the control unit, or at least connected to this. Thereby the control unit is enabled to detect the position of one or a plurality of slide tracks and to set the tool accordingly. Basically, fully automatic operation is also possible with this. Thus, for known geometrical data of the slip ring, optionally the precision of working can be increased with additional sensors. Similarly, high quality working can be achieved also without geometrical data.

It is especially advantageous when at least one sensor for detecting the quality of the surface of a side track is present. For example, a sensor of this kind can determine the contact resistance or also the roughness of the surface of a slide track. It is also possible to determine desired mechanical parameters such as round-running, bandwidth, depth of track, or also height and/or width of insulating ridges between the slide tracks. The values registered by the at least one sensor can be signaled to the control unit to control the working. Thus, for example, the slide track can be worked to an extent until a minimum given transition resistance has been attained, or until a predetermined surface condition, for example surface roughness, has been attained. Moreover, optionally a sensor for determining further parameters also can be provided. For example, this can test the insulating ridges between slide tracks, and transmit deviations to the control unit. Advantageously, a sensor of this kind comprises a camera.

The contact brushes which in the case of normal operation run on the slide tracks can be raised from the slide tracks during the working. This contributes particularly to protection of the brushes. Thus, no additional wear of the brushes is caused by briefly occurring unevenness of the slide track during the working. With working methods such as roller burnishing or grinding in which the roughness of the surface is reduced continuously, it is also possible to allow the brushes to rest against the slide track. Advantageously, in this case the contact or transition resistance between the brushes and the slide track is determined by means of the brushes. This can then be used for further control of the working. Thus, for example, the working can be terminated when the resistance falls below a lower limit value.

In another advantageous embodiment of the invention, the working is effected in at least two steps with at least two different tools. These can be, for example, different material cutting tools, or also a cutting tool in a first step, and a grinding tool in a second step. Similarly, for example, in a first step a rough removal of surface by means of a cutting tool, and in a second step a smoothing by means of a roller burnishing tool can be effected.

In particular with computer tomographs, it is often possible to tilt the rotating part of the gantry. Thus, for example, for working the slide tracks of a slip ring, the latter also can be tilted in order to achieve a certain pre-stressing of the gantry bearing and thus a specific position of the slip ring. Hereby, furthermore, a simplified removal of abraded matter or chips also can be achieved during the working. However, it is particularly advantageous to leave the slip ring in its normal operating position.

A device in accordance with the invention for performing the above-described method comprises a tool carrier for accommodating a tool for working the surface of the slip ring, and preferably of at least one slide track. Preferably the device comprises at least one suitable tool for working the surface of the slip ring, or of at least one slide track. Advantageously the tool carrier comprises at least one electrically or pneumatically controlled actuating drive for positioning the tool. Furthermore, optionally a control unit can be provided for controlling the actuating drive.

In an especially advantageous embodiment of the device according to the invention, an auxiliary drive is provided additionally for moving the slip ring relative to the tool carrier. Advantageously, an auxiliary drive of this kind can be mounted on the appliance, as already described previously. Preferably a means for accommodating this is provided on the appliance.

An appliance in accordance with the invention, in particular a computer tomograph, comprises a facility for accommodating a previously described device, in particular a tool carrier. Optionally, the appliance comprises an additional facility for accommodating an auxiliary drive. Furthermore, it comprises optionally a control unit for controlling the working. In another advantageous embodiment, it comprises a memory in which identification data for identifying the slip ring, and/or geometrical data of the slip ring are stored.

The term appliance as here used refers to an instrument or machine having a slip ring as a component part. The reference to an appliance with a slip ring in a built-in state relates to an appliance in which the slip ring is actually mounted for transmission of at least one electrical signal. It is not intended to mean that a slip ring is in a state of being clamped in a machine tool, such as for example a lathe.

In the preceding expositions reference is made to the working or machining of the surface of a slip ring. Basically, however, any desired region of the surface of a slip ring can be worked with a method according to the invention, and also with a device in accordance with the invention. Thus, for example, the supporting material and also the insulating material can be worked or machined. This is expedient, for example, when the surface of the insulating material has become damaged by intense formation of sparks. Here too, additional grooves for accommodating new slide tracks could be introduced to upgrade the slip ring. Because regions on the surface of the slip ring having minimal round-running tolerances can be produced with the method according to the invention, this can be applied specifically for the same purpose also during the fabrication. Thus, a support surface for a transmitter antenna of a non-contacting high-speed data line can be first worked according to the method of the invention, so that it will have a minimum radial deviation or axial run-out, depending upon assembly, along the direction of the antenna. Then, following the working, the antenna can be mounted. Furthermore, during application in the field, the method according to the invention can be used also to remove a defective antenna from the support of the slip ring, for example by machining down or grinding-down.

However, the preferred field of application of the method according to the invention and the device according to the invention is a re-working or re-machining, in particular for repair of the slide tracks.

In the following the invention will be described by way of example, without limiting the general inventive concept, on examples of embodiment and with reference to the drawings.

In FIG. 1 an example of a tool carrier with a tool, corresponding to the invention, is schematically illustrated. A gantry 1, to be described more fully later, of a computer tomograph comprises a stationary part 2 and also a rotating part 3. A slip ring 4 is attached to the rotating part 3. Slide tracks 5 are disposed on a surface of the slip ring 4. A device in accordance with the invention comprises a tool carrier 6 that is attached by means of a fastening element 11 to a fastening element 12 of the stationary part 2 of the gantry 1. The tool carrier 6 holds a tool 7 for working or machining the surface of the slip ring 4. In this example the tool 7 is a cutting tool. This is accommodated in a quick acting clamp device 8. The tool is adapted to be movable in an axial and a radial direction relative to the surface of the slip ring. An actuating drive 9 is provided for positioning the tool along an axial direction Y. Another actuating drive 10 makes possible a positioning of the tool along a radial direction X relative to the rotating part of the gantry and thus also to the slip ring. Here, for example, both actuating drives have a driving motor for rotating a spindle for moving a carriage. In a preferred manner, position sensors such as linear path encoders or also angle encoders are also provided in order to detect an exact position of the carriage and thus of the tool. In the example of embodiment shown here, the actuating drive 10 is first disposed on the fastening element 11. Onto the carriage of this actuating drive, the second actuating drive 9 is then fastened. Here, therefore, the complete second actuating drive is moved in radial direction X. Furthermore, the tool 7 is fastened onto the carriage of the second actuating drive 9 by means of a quick acting clamp device 8. Because of the simple manner of attachment of the entire tool carrier to the fastening element 12 of the stationary part of the gantry by means of the fastening element 11, the tool carrier can be removed in a simple way and manner, for example by loosening the screws shown here. Advantageously, additional positioning aids such as stoppers, pins or others for exact alignment and adjustment of the two fastening elements, and thus also of the tool holder 6 with respect to the gantry 1, are further provided on the fastening element 11 and/or on the fastening element 12.

Figure 2:
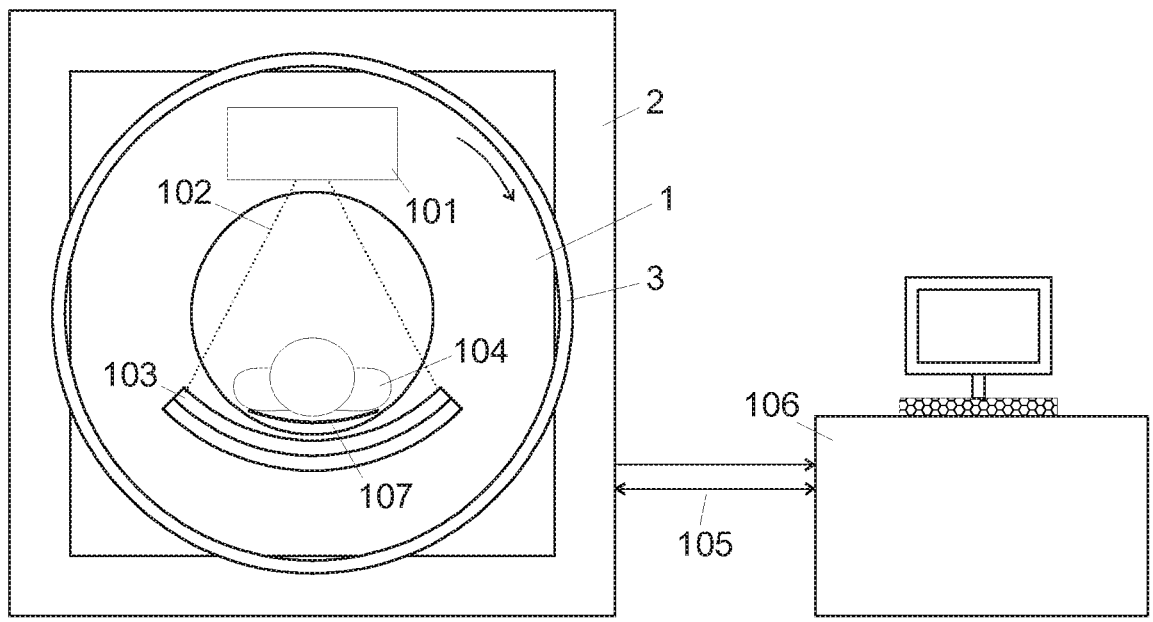
FIG. 2 shows a computer tomograph.

FIG. 2 shows a device in accordance with the invention, using a computer tomograph as an example. The computer tomograph (CT scanner) consists of two main mechanical components. A stationary part 2 serves as a base and frame of the entire appliance, in which the rotating part 1 revolves. A patient 104 is positioned on a berth 107 within an opening of the rotating part. An X-ray tube 101 and an oppositely disposed detector 103 are provided for scanning the patient by means of X-rays 102. An X-ray tube 101 and a detector 103 are disposed to be rotatable on the rotating part 1. A rotary joint 3 serves as an electrical link between the rotating part 1 and the stationary part 2. Hereby high electric power for feeding the X-ray tube 101 is transmitted in a direction of the rotating part 1, and at the same time raw image data are transmitted in an opposite direction. Communication of control data in both directions is provided in parallel with this. An evaluation and control unit 106 serves for operating the computer tomograph, and also for displaying the generated images. The communication with the computer tomograph is effected via a bidirectional link 105.

The invention claimed is:

1. A method for repairing or reconditioning a slip ring built into an appliance for normal operation, by working or machining at least partly a surface of the slip ring whilst the slip ring remains in its built-in state in the appliance, comprising the following steps:
   (a) mounting a tool carrier having a tool for machining the surface of the slip ring on the appliance;
   (b) rotating the slip ring relative to the tool carrier; and
   (c) machining the surface of the slip ring with the tool.

2. The method according to claim 1, wherein the tool used for machining the surface of the slip ring is at least one of a material-removing cutting tool, a grinding tool, and a tool for shaping or deforming the surface.

3. The method according to claim 1, wherein the slip ring is rotated with a drive used for normal operation of the appliance.

4. The method according to claim 1, wherein the slip ring is rotated with an auxiliary drive.

5. The method according to claim 1, wherein a rotational speed of the slip ring is controlled for adaptation to a machining operation.

6. The method according to claim 1, wherein a position of the tool for machining is controlled by means of a control unit.

7. The method according to claim 1, wherein a position of the tool for machining is controlled taking into account geometrical data of the slip ring as stored in a memory.

8. The method according to claim 1, wherein at least one slide track on the slip ring is machined, and a position of the tool for machining is controlled while detecting by means of at least one sensor at least one of a position and a dimension of the at least one slide track to be machined.

9. The method according to claim 1, wherein a transition or contact resistance between a slide track being machined and slide brushes provided for normal operation of the appliance is measured, and machining of the slide track is terminated when the transition or contact resistance drops to below a given limiting value.

\* \* \* \* \*